United States Patent [19]

Pfirrmann

[11] Patent Number: 4,772,468
[45] Date of Patent: Sep. 20, 1988

[54] CHEMICAL COMPOSITIONS

[75] Inventor: Rolf W. Pfirrmann, Lucerne, Switzerland

[73] Assignee: ED Geistlich Sohne AG Fur Chemische Industrie, Lucerne, Switzerland

[21] Appl. No.: 105,998

[22] Filed: Oct. 7, 1987

Related U.S. Application Data

[63] Continuation of Ser. No. 882,227, Jul. 7, 1986, which is a continuation of Ser. No. 662,886, Oct. 19, 1984, abandoned.

[30] Foreign Application Priority Data

Oct. 20, 1983 [GB] United Kingdom ................. 8328074

[51] Int. Cl.⁴ ............................................. A61K 33/42
[52] U.S. Cl. ..................................................... 424/128
[58] Field of Search ......................................... 424/128

[56] References Cited

U.S. PATENT DOCUMENTS 3,075,880  1/1963  Roth .................................... 424/128
4,477,439 10/1984  D'Alelio ............................. 424/128

FOREIGN PATENT DOCUMENTS 0008052  2/1980  European Pat. Off. ............ 424/128
2905878  8/1980  Fed. Rep. of Germany ...... 424/128

OTHER PUBLICATIONS

Chemical Abstracts, 98:149498z, Erb et al. (1982).
Chemical Abstracts, 98:59964u, Eitenmueller (1982).
Chemical Abstracts, 97:223006k (1982).

*Primary Examiner*—Allen J. Robinson
*Assistant Examiner*—John M. Kilcoyne
*Attorney, Agent, or Firm*—Bernard, Rothwell & Brown

[57] ABSTRACT

The invention provides a pharmaceutical composition for filling into bone cavities comprising an agueous paste formed from powdered calcium phosphate and an antibacterial substance, if necessary together with one or more binders. The antibacterial substance is preferably taurolidine and the calcium phosphate is preferably β-tricalcium phosphate.

9 Claims, No Drawings

CHEMICAL COMPOSITIONS

This is a continuation of application Ser. No. 882,227, filed July 7, 1986, now abandoned, which is a continuation of application Ser. No. 662,886, filed Oct. 19, 1984, and also now abandoned.

This invention relates to a novel composition of use in the treatment of osteitis and osteomyelitis.

In the treatment of osteitis and osteomyelitis, where infection has led to necrosis of bone, it is essential that the necrotic bone (sequester) is removed from the infected site before further treatment can take place. Relatively large cavities are formed in this way and the regeneration of the bone tissue, including the spongeosa, is the primary objective of such further treatment. In our European Patent Application No. 48558 we have described resorbable gel formulations (which may contain antibacterial substances and other materials which assist bone regeneration and prevent re-infection) to be inserted in granulated form into such cavities to promote tissue growth.

In our above patent application we described gel formulations which contained up to about 20% by weight of calcium phosphate to provide calcium and phosphorus needed for bone formation. However, the granulated gel provided the main bulk of material required to fill the cavity, the voids between the gel granules permitting new tissue to grow into the mass which is gradually resorbed. Eventually, all the gel resorbed and the cavity is filled by bone tissue. Even calcium phosphate is largely resorbed and regenerated in the physiological form in the new bone.

We have now found that an alternative composition for filling into bone cavities of human or animal subjects resulting from the surgical treatment of osteomyelitis and osteitis comprises an aqueous paste formed from powdered resorbable calcium phosphate and an antibacterial substance resorbable together with one or more binders.

The calcium phosphate may be secondary or tertiary calcium phosphate or a more complex form such as hydroxyapatite. Other forms of calcium phosphate which can be used include tetra calcium phosphate and octa calcium phosphate. Tertiary calcium phosphate (i.e. tricalcium phosphate) is preferably in the $\beta$-form since this has been found to be more compatible with the growing bone cells and is more efficiently resorbed than the $\alpha$-form. The particle size of the calcium phosphate is preferably above 200 microns, for example in the range 200-500 microns.

The preferred form of calcium phosphate is thus $\beta$-tricalcium phosphate in substantially pure form. The purity of the product can be determined by X-ray diffraction; however small quantities up to 2.3% of the $\alpha$-form may be undetectable.

The antibacterial substances employed may be antibiotics and other microbiocidal or microbiostatic substances. In addition, further medicaments, for example analgesic agents may be used. In addition, the compositions can also contain other dissolved additives which promote healing of the wound and/or favourably influence the physical and biochemical properties of the composition. These are, for example, amino acids, sugar, polyhydric alcohols, common salt and others.

When the antibacterial substance is an antibiotic, it is preferably a broad spectrum antibiotic active against both gram-negative and gram-positive bacteria, for example, a $\beta$-lactam antibiotic such as a penicillin or cephalosporin, a tetracycline antibiotic, a macrolide antibiotic such as erythromycin, a polypeptide antibiotic such as bacitracin, novobiocin, or, more preferably, an aminoglycoside antibiotic such as streptomycin, neomycin, lincomycin, kanamycin, vancomycin, gentamicin or sisomycin. Typical infecting bacteria include *Staphylococcus aureus*, Proteus, Pseudomonas, Streptococcus, *E. coli*, as well as Enterococci, Klebsiella and *Staphylococcus albus*. However, antibiotics are often contraindicated for use in surgical treatment, due to their tendency to produce resistant strains, and a preferred type of antibacterial substance is a methylol transfer agent, especially noxytiolin or, more preferably taurolidine or a close analogue thereof. Taurolidine is bis-(1,1-dioxo-perhydroxy-1,2,4-thiadiazin-4-yl)methane and this compound and its close analogues can be represented by the formula:

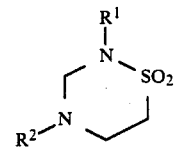

where $R^1$ is hydrogen or a methyl, ethyl, propyl, butyl or pentyl group and $R^2$ is hydrogen or a group

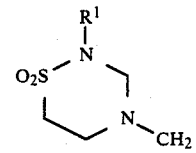

where $R^1$ has the above meaning. Where $R^1$ and $R^2$ are both hydrogen, the compound is the methylol transfer antibacterial taurultam.

The preferred active substances are broad spectrum antibiotics and methylol transfer agents such as taurolidine. Taurolidine and its analogues are active against both gram-negative and gram-positive organisms, as well as against the toxins produced by gram-negative bacteria.

The complex of elemental iodine and polyvinyl pyrrolidone may also be advantageously be used as a microbiocidal substance.

It is important that the binder for the calcium phosphate should be resorbable, so that it does not remain and give rise to tissue reactions after the remains of the composition has been resorbed.

In general, polyvinylpyrrolidone can be used as a binder in the formulations. A molecular weight in the range of 200-30,000 is preferred. Kollidone 17 (sold by BASF) is one suitable form. Other useful binding agents include gelatin, e.g. edible gelatin, and dextran; the molecular weight of the dextran is preferably about 70,000. The binding agent will commonly comprise 2-10% by weight of the composition e.g. 4-6%.

The compositions of the invention will normally contain a relatively large amount of water, e.g. in the range of 30-60%, preferably 40-50%. In general, the proportions of water and binding agent will depend on the consistency which is required. Relatively fluid compositions may be useful in that they can be introduced into the cavity via a post-operative drainage tube. In other instances, however, it may be preferable to pack the cavity with a more solid composition before closing the wound.

The quantity of calcium phosphate in the compositions will in general be above 30% and preferably about 40% by weight, they will normally contain up to 60% or even up to 70% by weight. This contrasts with the quantities of calcium phosphate incorporated into the gels as described in our above patent application which were always less than 20%.

The quantity of antibacterial substance may conveniently be in the range 0.5–5% by weight. Where taurolidine is used, it is preferably present in the range 1–4% by weight. In large cavities, 2% taurolidine may be sufficient; in small cavities, e.g. in bones in the wrist, 4% by weight of taurolidine is preferred.

The following Examples are given by way of illustration only:

EXAMPLE 1

|  | Weight % |
| --- | --- |
| β-Tricalcium phosphate (200 microns) | 40,00 |
| Taurolidine | 4,00 |
| Kollidone 17 PF | 5,00 |
| Distilled water | 51,00 |

The above components are blended to give a relatively fluid suspension which can be administered via a drainage tube.

EXAMPLE 2

|  | Weight % |
| --- | --- |
| β-Tricalcium phosphate | 50,00 |
| Taurolidine | 4,00 |
| Kollidone 17 PF | 5,00 |
| Distilled water | 41,00 |

The above components were blended together to yield a thick but still fluid paste which could be administered via a drainage tube and would remain in the cavity.

EXAMPLE 3

|  | Weight % |
| --- | --- |
| β-Tricalcium phosphate | 50,00 |
| Taurolidine | 4,00 |
| Dextran 70,000 | 5,00 |
| Distilled water | 41,00 |

The above components were blended together to give a relatively thick but fluid paste which could be introduced into a bone cavity via a drainage tube or directly, and would remain in the cavity.

EXAMPLE 4

|  | Weight % |
| --- | --- |
| Tricalcium phosphate | 55,00 |
| Taurolidine | 4,00 |
| Dextran 70,000 | 5,00 |
| Distilled water | 36,00 |

The above components were blended together to provide a plastic paste particularly suitable for direct application into an open cavity.

EXAMPLE 5

|  | Weight % |
| --- | --- |
| Dicalcium phosphate | 50,00 |
| Dextran 70,00 | 5,00 |
| Taurolidine | 4,00 |
| Distilled water | 41,00 |

The above components were blended together to give a rather fluid suspension.

EXAMPLE 6

|  | Weight % |
| --- | --- |
| Dicalcium phosphate | 60,00 |
| Dextran 70,000 | 5,00 |
| Taurolidine | 4,00 |
| Distilled water | 31,00 |

The above components were blended together to give a relatively thick paste.

I claim:

1. A pharmaceutical composition for filling bone cavities via a drainage tube comprising a fluid aqueous paste comprising from 40% to 70% by weight of powdered, substantially pure β-tricalcium phosphate as determined by X-ray diffraction, an antibacterially effective amount of an antibacterial substance and at least one resorbable binder.

2. A composition as claimed in claim 1, wherein the antibacterial substance is present in an amount from 0.5% to 5% by weight.

3. A composition as claimed in claim 1, wherein the antibacterial agent is taurolidine and it is present in an amount from 1% to 4% by weight.

4. A composition as claimed in claim 1 in which the resorbable binder comprises at least one material selected from the group consisting of polyvinylpyrrolidone, gelatin and dextran.

5. A composition as claimed in claim 1, wherein the binding agent is present in an amount from 2% to 10% by weight.

6. A composition as claimed in claim 1, wherein the binding agent is present in an amount from 4% to 6% by weight.

7. A composition as claimed in claim 1, further comprising from 30% to 60% by weight of water.

8. A composition as claimed in claim 1, further comprising from 40% to 50% by weight of water.

9. A method of filling a bone cavity in a human or animal subject wherein a composition as claimed in claim 1 is introduced into said cavity.

* * * * *